US005596085A

United States Patent [19]
Silver et al.

[11] Patent Number: 5,596,085
[45] Date of Patent: Jan. 21, 1997

[54] METHOD FOR PREPARING POLYOL FATTY ACID POLYESTERS BY TRANSESTERIFICATION

[75] Inventors: Richard S. Silver, Wilmette; Gerard L. Hasenhuettl, Deerfield, both of Ill.

[73] Assignee: Kraft Foods, Inc., Northfield, Ill.

[21] Appl. No.: 420,065

[22] Filed: Apr. 11, 1995

[51] Int. Cl.$^6$ ............................. C07H 15/00; C07H 15/06
[52] U.S. Cl. ........................ 536/18.6; 536/18.5; 536/119
[58] Field of Search ........................ 536/18.5, 18.6, 536/119

[56] References Cited

U.S. PATENT DOCUMENTS

| | | | |
|---|---|---|---|
| 2,853,485 | 9/1958 | Werner et al. | 260/234 |
| 2,893,990 | 7/1959 | Hass et al. | 260/234 |
| 2,931,802 | 4/1960 | Touey et al. | 260/234 |
| 2,938,898 | 5/1960 | Werner et al. | 260/209 |
| 2,948,717 | 8/1960 | Babayan et al. | 260/234 |
| 3,057,743 | 10/1962 | Touey et al. | 106/169 |
| 3,059,009 | 10/1962 | Schmid et al. | 260/428 |
| 3,059,010 | 10/1962 | Schmid et al. | 260/428 |
| 3,096,324 | 7/1963 | Goins et al. | 260/234 |
| 3,248,381 | 4/1966 | Nobile et al. | 260/234 |
| 3,251,827 | 5/1966 | Schnell et al. | 260/234 |
| 3,353,966 | 11/1967 | Hugenberg et al. | 99/163 |
| 3,378,542 | 4/1968 | O'Boyle | 260/210 |
| 3,480,616 | 11/1969 | Osipow et al. | 260/234 |
| 3,597,417 | 3/1971 | Myhre | 536/119 |
| 3,792,041 | 2/1974 | Yamagishi et al. | 260/234 R |
| 3,954,976 | 5/1976 | Mattson et al. | 424/180 |
| 3,963,699 | 6/1976 | Rizzi et al. | 260/234 R |
| 4,005,196 | 1/1977 | Jandacek et al. | 424/180 |
| 4,034,083 | 7/1977 | Mattson | 424/180 |
| 4,104,464 | 8/1978 | James | 536/115 |
| 4,241,054 | 12/1980 | Volpenhein et al. | 424/180 |
| 4,244,882 | 1/1981 | Isa et al. | 260/410.6 |
| 4,264,583 | 4/1981 | Jandacek | 424/240 |
| 4,298,730 | 11/1981 | Galleymore et al. | 536/119 |
| 4,334,061 | 6/1982 | Bossier, III | 536/119 |
| 4,368,213 | 1/1983 | Hollenbach et al. | 426/590 |
| 4,377,685 | 3/1983 | Bouniot et al. | 536/119 |
| 4,382,924 | 5/1983 | Berling et al. | 424/180 |
| 4,446,165 | 5/1984 | Roberts | 426/602 |
| 4,461,782 | 7/1984 | Robbins et al. | 426/549 |
| 4,517,360 | 5/1985 | Volpenhein | 536/119 |
| 4,518,772 | 5/1985 | Volpenhein | 536/119 |
| 4,611,055 | 9/1986 | Yamamoto et al. | 536/119 |
| 4,675,393 | 6/1987 | Coxon | 536/18.6 |

(List continued on next page.)

FOREIGN PATENT DOCUMENTS

| | | |
|---|---|---|
| 0062565 | 10/1982 | European Pat. Off. |
| 0252250 | 1/1988 | European Pat. Off. |
| 0311154 | 4/1989 | European Pat. Off. |
| 0320043A2 | 4/1989 | European Pat. Off. |
| 0349058A2 | 1/1990 | European Pat. Off. |
| WO92/03060 | 3/1992 | European Pat. Off. |
| 156263 | 8/1982 | Germany. |
| 227137A1 | 9/1985 | Germany. |
| 262663A1 | 12/1988 | Germany. |

| | | |
|---|---|---|
| WO92/00947 | 1/1992 | WIPO. |

OTHER PUBLICATIONS

Bailey, "Bailey's Industrial Oil & at Products", 1964, pp. 958–972.

Mieth, et al. "Zur Synthese und Charakterisierung von Saccharosefettsäurepolyestern 1. Mitt. Über Ein Neues Syntheseverfahren," taken from *Die Nahrung* 27.8 (1983) pp. 747–751. (No translation).

Akoh, et al., "Preparation of Trehalose and Sorbitol Fatty Acid Polyesters by Intersection," *JAOCS*, vol. 66, No. 11, (Nov. 1989), pp. 1581–1587.

Akoh, et al., "Optimized Synthesis of Sucrose Polyesters: Comparison of Physical Properties of Sucrose Polyesters, Raffinose Polyesters and Salad Oils," *Journal of Food and Sciences*, vol. 55, No. 1, 1990.

Akoh, et al., "Synthesis and Properties of Alkyl Glycoside and Stachyose Fatty Acid Polyesters," *JAOCS*, vol. 66, No. 9 (Sep. 1989), pp. 1295–1301.

Akoh, et al., "One–Stage Synthesis of Raffinose Fatty Acid Polyesters," Journal of Foods and Science, vol. 52, No. 6, (1987).

Linstead, et al. "The Stable form of Sucrose Octaacetate," *J. Amer. Chem. Soc.*, 62, 3260 (1940).

A. Elsner, et al., "Zur Synthese und Charakterisierung von Saccharosefettsäure–Polyestern 3. Mitt. Verfahren zur Herstellung grenzflächenaktiver Verbindungen," *Die Nahrung*, vol. 33, No. 9, pp. 845–851 (1989) (No translation).

G. Mieth, et al., "Zur Synthese und Charakterisierung von Saccharose fettsäurepolyestern 2. Mitt. Modifizierung des Syntheseverfahrens von Saccharosefettsäuretotalestern zur Gewinnung eines grenzflächenaktiven Pseudofettyps," *Die Nahrung*, vol. 33, No. 6, pp. 517–575 (1989) (No translation).

R. U. Lemieux, et al., "The Preparation of Sucrose Monoesters," *Canadian Journal of Chemistry*, vol. 40, pp. 2376–2392 (1962).

*Primary Examiner*—John Kight
*Assistant Examiner*—Howard C. Lee
*Attorney, Agent, or Firm*—Fitch, Even, Tabin & Flannery

[57] ABSTRACT

An improved method for the preparation of polyol fatty acid polyesters via a one step reaction. A polyol-type reagent is mixed with a fatty-acid containing reagent, and an esterification catalyst to form a reaction mixture. The polyol-type reagents include polyols and saccharides having hydroxyl groups, partially-esterified polyols and saccharides having both hydroxyl groups and lower alkyl ester groups, and fully-esterified polyols and saccharides having lower alkyl ester groups. The reaction is heated to about 95° to 200° C. for a time sufficient for the formation of saccharide fatty acid polyester while a non-fatty acid-containing lower alkyl ester by-product or an alcohol by-product are removed from the reaction mixture by a thin film reaction techniques. The use of thin film reaction methodology provides more efficient removal of by-products and greater yields of the polyol fatty acid polyesters. The polyol fatty acid polyesters, especially sucrose fatty acid polyesters, are useful as fat substitutes or low-calorie fats in food compositions.

21 Claims, No Drawings

U.S. PATENT DOCUMENTS

| | | | |
|---|---|---|---|
| 4,683,299 | 7/1987 | Kea et al. | 536/119 |
| 4,806,632 | 2/1989 | McCoy et al. | 536/124 |
| 4,840,815 | 6/1989 | Meyer et al. | 426/611 |
| 4,877,871 | 10/1989 | Klemann et al. | 536/124 |
| 4,897,474 | 1/1990 | Bickert | 536/119 |
| 4,931,552 | 6/1990 | Gibson et al. | 536/119 |
| 4,942,054 | 7/1990 | Winter et al. | 426/611 |
| 4,942,228 | 7/1990 | Gibson | 536/119 |
| 4,954,621 | 9/1990 | Masaoka et al. | 536/119 |
| 4,966,966 | 10/1990 | Wada et al. | 536/119 |
| 4,968,791 | 11/1990 | Van Der Plank | 536/119 |
| 4,973,489 | 11/1990 | Meyer et al. | 426/611 |
| 4,973,682 | 11/1990 | Willemse | 536/119 |
| 5,006,648 | 4/1991 | Van der Plank et al. | 536/119 |
| 5,008,387 | 4/1991 | Matsumoto et al. | 536/119 |
| 5,043,438 | 8/1991 | Buter | 536/119 |
| 5,055,571 | 10/1991 | Van Lookeren | 536/124 |
| 5,071,975 | 12/1991 | Van der Plank et al. | 536/119 |
| 5,079,355 | 1/1992 | Grechke et al. | 536/119 |
| 5,144,023 | 9/1992 | Willemse | 536/124 |
| 5,158,796 | 10/1992 | Bernhardt et al. | 426/549 |
| 5,194,281 | 3/1993 | Johnston et al. | 426/531 |
| 5,225,049 | 7/1993 | Barmentlo et al. | 203/34 |
| 5,231,199 | 7/1993 | Willemse | 554/174 |
| 5,239,097 | 8/1993 | Wolf et al. | 554/190 |
| 5,250,155 | 10/1993 | Zwanenburg et al. | 203/34 |

METHOD FOR PREPARING POLYOL FATTY ACID POLYESTERS BY TRANSESTERIFICATION

FIELD OF THE INVENTION

This invention provides an improved method for the preparation of polyol fatty acid polyesters, especially sucrose fatty acid polyesters, via a process involving intermolecular esterification and transesterification reactions of lower alkyl ester and/or hydroxyl groups of a polyol-type reagent (i.e., glycosides, reducing saccharides, polyols, and lower alkyl esterified saccharides) with a fatty acid-containing reagent (i.e., fatty acids, fatty acid esters, salts of fatty acids, fatty acid anhydrides, and fatty acid halides). The improved method of this invention allows for the preparation of polyol fatty acid polyesters with less caramelization and with less generation of low molecular weight ester by-products. The reduction of caramelization allows for the formation of products having better (i.e., lighter) color characteristics. The reduction in low molecular weight by-products reduces the amount of waste material which must be disposed of or treated for recycling. The improved method of this invention provides for a more efficient production of polyol fatty acid polyesters, since the by-products of the reaction are removed more rapidly and efficiently by thin film reaction methodology. The sucrose fatty acid polyesters produced by the improved method of this invention are especially useful as fat substitutes in food applications and products.

BACKGROUND OF THE INVENTION

A major nutritional problem in the United States today is obesity. Obesity generally results from the consumption of more calories than are expended, and fats contribute from 30% to 40% of the calories consumed by most Americans. Consumption of fat contributes to human disease states, such as heart and coronary disease. One method of reducing obesity and/or diseases such as heart and coronary diseases in the human population is to reduce the consumption of fat. In recent years, fat substitutes or low-calorie fats have attracted increasing attention as a method of reducing the fat and calorie content of foodstuffs. The objective is to provide edible fats with reduced absorption and digestive properties with minimal side effects and with acceptable taste and feel characteristics when incorporated into food compositions.

Transesterification reactions have been used to prepare saccharide fatty acid polyesters which have reduced absorption and digestive properties. Such transesterification reactions generally required high temperatures and/or toxic solvents (such as dimethyl acetamide, dimethyl formamide, dimethyl sulfoxide, and the like) and were not, therefore generally suitable for the preparation of fat substitutes for use in food applications. Another method for the production of sucrose fatty acid esters is the "micro-emulsion" process. A drawback of that process is that it is difficult to remove the solvent used while maintaining the micro-emulsion state. In addition, large quantities of soap are also required to produce stable micro-emulsions.

Rizzi et al., U.S. Pat. No. 3,963,699 (issued Jun. 15, 1976), provided a solvent-free process for the production of saccharide fatty acid polyesters. The method involved heating sucrose, fatty acid lower alkyl esters, an alkali metal fatty acid soap, and a basic catalyst to form a homogeneous melt at 185° C. or greater. Thereafter, excess fatty acid lower alkyl esters are added in the second step to the reaction product of the first step. One drawback to this method is that after only a few moments at 185° C. or above, sucrose begins to decompose which leads to undesirable by-products. Another drawback is that this reaction mixture of Rizzi et al. is heterogeneous due to the mutual insolubility of sucrose and the fatty acid lower alkyl esters.

Akok and Swanson, 55 *J. Food Sci.*, 236 (1990), employed sucrose octaacetate rather than sucrose in a transesterification reaction. Sucrose octaacetate has increased solubility in the fatty acid ester reactants and, therefore, provides a more homogeneous reaction system along with better yields of the sucrose fatty acid polyester and lighter colored products (i.e. reduced caramelization and other decomposition reactions.) This method results in the generation of large amounts of non-fatty acid-containing ester. (Eight moles of methyl acetate are produced for each mole of sucrose octaacetate reacted.) Methyl acetate is a highly flammable material which generally must be either disposed of in an environmentally acceptable manner or converted to acetic acid for reuse or recycling.

Yamamoto et al., U.S. Pat. No. 4,611,055 (issued Sep. 9, 1986), provided a method whereby the sucrose fatty acid esters are purified by subjecting the acidified reaction product to molecular distillation whereby the sucrose fatty acid polyesters are recovered as the residue. In the reaction, Yamamoto et al. called for a molten mixture of sucrose, a fatty acid lower alkyl ester, a basic transesterification catalyst, and a fatty acid alkali metal soap at a temperature from 120° to 180° C. under a vacuum less than 10 mm Hg with stirring. In that reaction, the fatty acid alkali metal soap is used to insure a homogeneous reaction mixture. Such fatty acid metal soap is not used or required in the Meyer et al. method discussed below.

More recently, Meyer et al., U.S. Pat. No. 4,840,815 (issued Jun. 20, 1989) and Meyer et al., PCT Publication WO 92/03060 (published Mar. 5, 1992), provided a one-stage, solvent-free, low-temperature, low-pressure process for the preparation of saccharide fatty acid polyesters. The Meyer et al. process involves reacting a mixture of a lower acyl ester saccharide, a fatty acid lower alkyl ester, and an alkali metal catalyst at a reaction temperature of 100° to 125° C. while drawing a vacuum of less than about 15 torr over the reaction mixture. The saccharide fatty acid polyesters are reported to be formed via a transesterification reaction whereby at least a portion of the lower acyl ester groups on the starting saccharide are replaced with the fatty acid groups from the fatty acid lower alkyl ester. The transesterification catalysts employed were alkali metals, with sodium and potassium metals the most preferred. At the reaction temperature, the alkali metal catalysts were molten.

The assignee of the present application has filed two other applications each entitled, "Improved Method for Preparing Saccharide Fatty Acid Polyesters By Transesterification," Ser. Nos.: 08/132,106, filed Oct. 5, 1993 and 08/132,497, filed Oct. 5, 1993. Those applications are incorporated by reference here. Those applications disclose reactions for generating saccharide fatty acid polyesters, although they have the drawback that removal of by-products is not as effective as desired. The instant invention comprises the further inventive step of requiring the use of thin film reaction methodology to facilitate removal of the non-fatty acid-containing ester and/or alcohol by-products, thereby increasing the efficiency of the reaction to produce polyol fatty acid polyesters.

It is desirable to provide a new method for the production of polyol fatty acid polyesters, especially sucrose fatty acid polyesters, which overcomes some of the problems encountered in the prior art. It is also desirable to provide a new method for the production of polyol fatty acid polyesters, especially sucrose fatty acid polyesters, which results in less caramelization and/or decomposition products and which generates reduced amounts of by-product low molecular weight esters and/or alcohols. The methods of the present invention are generally easier to use and provide better polyol fatty acid polyesters than the methods of the prior art. The methods of the present invention generally result in less caramelization and better yields of the polyol fatty acid polyesters as the reaction by-products are removed more efficiently in a thin film reaction, thereby resulting in more efficient formation of polyol fatty acid polyester by forcing the fatty acid esterification equilibrium reaction towards completion.

SUMMARY OF THE INVENTION

This invention provides an improved method for the preparation of polyol fatty acid polyesters, especially sucrose fatty acid polyesters, via a process involving intermolecular esterification and transesterification reactions of the lower alkyl ester and/or hydroxyl groups of a polyol-type reagent with a fatty acid-containing reagent. For purposes of this invention, a "polyol-type reagent" includes polyols and saccharides containing hydroxyl groups, partially-esterified polyols and saccharides containing both hydroxyl groups and lower alkyl ester groups, and fully-esterified polyols and saccharides containing lower alkyl ester groups. The lower alkyl ester groups of the partially- and fully esterified polyols and saccharides contain alkyl groups having 1 to 6 carbon atoms. For purposes of this invention, a "fatty-acid containing reagent" includes fatty acids, fatty acid anhydrides, and fatty acid halides. The fatty acid lower alkyl esters contain lower alkyl groups of 1 to 6 carbon atoms; preferably the lower alkyl groups is methyl. The improved method of this invention allows for the preparation of saccharide fatty acid polyesters with less caramelization and reduced generation of low molecular weight ester and/or alcohol by-products. The reduction of caramelization allows for the formation of products having better (i.e., lighter) color characteristics. The reduction in low molecular weight ester and/or alcohol by-products reduces the amount of waste material which must be disposed of or treated for recycling. The improved method of this invention provides for a more efficient production of polyol fatty acid polyesters, since the by-products of the reaction are removed by thin layer reaction methodology. The sucrose fatty acid polyesters produced by the improved method of this invention are especially useful as fat substitutes in food applications and products.

The improved process of the present invention involves reacting a polyol-type reagent with a fatty acid-containing reagent whereby essentially all or most of the hydroxyl or ester groups in the polyol-type reagent are replaced with fatty acid ester groups to form a saccharide fatty acid polyester. The transesterification reaction is generally carried out at temperatures of from about 95° to 200° C. under essentially anhydrous conditions. The improved process of the present invention involves removing the relatively low molecular weight, non-fatty acid-containing lower alkyl ester by-product and/or alcohol by-product by thin film reaction methodology to drive the reaction equilibrium towards the formation of the desired polyol fatty acid polyester.

The general reactions can be illustrated by the following general reaction scheme using a lower alkyl esterified saccharide as the polyol-type reagent and a fatty acid lower alkyl ester (i.e., R'COOR") as the fatty-acid containing reagent:

Optional Esterification Reaction:

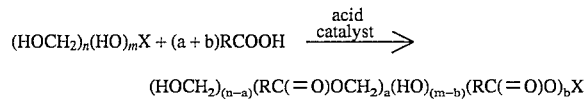

Transesterification Reaction:

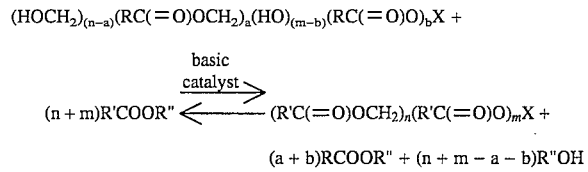

where RC(=O)— represents a lower acyl group where R is an alkyl group having 1 to 6 carbon atoms, X represents the saccharide backbone, n is the number of hydroxyl groups on the primary carbons in the saccharide backbone, m is the number of hydroxyl groups on the secondary carbons of the saccharide backbone, a is the number of lower acyl groups on primary carbons in the partially esterified saccharide, b is the number of lower acyl groups on secondary carbons in the partially esterified saccharide, the average of the sum (a+b) is at least 1, R' is a saturated or unsaturated long chain aliphatic group preferably derived from a fatty acid, and R" is a lower alkyl group having 1 to 6 carbon atoms. In the improved process of the invention, use of thin film reaction methods facilitate the removal of the by-products RCOOR" and R"OH from the reaction mixture of the transesterification reaction to drive the equilibrium towards the desired saccharide fatty acid polyester product $(R'COOCH_2)_n(R'COO)_mX$. The reaction schemes using the other polyol-type reagents and fatty acid-containing reagents would be similar to the one described above taking into account the different structures of the polyol-type reagents and the fatty acid-containing reagents.

Preferably the saccharide is sucrose and both R and R" are methyl groups, in which case the by-product RCOOR" is methyl acetate, the by-product R"OH is methanol, and the product $(R'COOCH_2)_n(R'COO)_mX$ is sucrose fatty acid polyester. Of course, as one skilled in the art will realize, the by-product methanol is produced by fatty acid esterification of hydroxyl groups and the by-product methyl acetate is produced by fatty acid transesterification of acetate groups in the saccharide. Both types of by-products will be produced in a given reaction if a partially-esterified saccharide is used. The by-products methyl acetate and methanol are removed from the reaction mixture to drive the equilibrium to the right hand side of the transesterification equation and towards formation of the saccharide fatty acid polyester by thin film reaction methodology.

One object of the present invention is to provide a method for making a polyol fatty acid polyester comprising:

(1) mixing a polyol-type reagent, a fatty acid-containing reagent, and an esterification catalyst under essentially anhydrous conditions to form a reaction mixture; and (2) heating the reaction mixture to about 95° to 200° C. for a time sufficient to form the polyol fatty acid polyester while removing non-fatty acid-containing lower alkyl ester by-product or alcohol by-product from the reaction mixture wherein the reaction mixture is maintained in a thin film to facilitate removal of the by-product.

Another object of the present invention is to provide a method for making a saccharide fatty acid polyester comprising:

(1) esterifying one or more hydroxyl groups of a saccharide to form a partially-esterified saccharide having at least one lower alkyl ester group or a fully-esterified saccharide having lower alkyl ester groups;

(2) mixing the partially-esterified saccharide or fully-esterified saccharide, a fatty acid-containing reagent, and an esterification catalyst under essentially anhydrous conditions to form a reaction mixture; and (3) heating the reaction mixture to about 95° to about 200° C. for a time sufficient to form the saccharide fatty acid polyester while removing a non-fatty acid-containing lower alkyl ester by-product or alcohol by-product from the reaction mixture, wherein the reaction mixture is maintained in a thin film to facilitate removal of the by-product.

DETAILED DESCRIPTION OF THE PREFERRED EMBODIMENT

The method of the present invention provides an improved method for the preparation of polyol fatty acid polyesters. In the present method, a polyol-type reagent is subjected to an esterification or transesterification reaction. The polyol-type reagent is subjected to an esterification and/or transesterification reaction with a fatty acid-containing reagent whereby the lower alkyl ester groups and/or hydroxyl groups of the polyol-type reagent are essentially replaced with fatty acid ester groups to yield a polyol fatty acid polyester. Using a lower alkyl esterified saccharide, the reactants will generally form a homogeneous reaction mixture at the transesterification reaction temperature. The relatively low molecular weight, non-fatty acid-containing lower alkyl ester by-product and/or the alcohol by-product will be removed by thin layer reaction techniques during the transesterification reaction in order to drive the reaction equilibrium towards completion and the formation of the desired saccharide fatty acid polyester. Using such lower alkyl esterified saccharides yields on the order of about 80 to 99 percent can be obtained with reaction times of about four hours.

The lower alkyl esterified saccharide can be prepared by conventional means which allow for esterification of the hydroxyl groups of a saccharide. Preferably, the lower alkyl esterified saccharide is sucrose octaacetate, which contains eight acetate groups. Conventional esterification methods for preparing lower alkyl esterified saccharides are described in Linstead et al., *J. Amer. Chem. Soc.*, 62, 3260 (1940) and Coxon, U.S. Pat. No. 4,675,393, both of which are hereby incorporated by reference. The "lower alkyl ester" groups are ester groups of formula RC(=O)O— where R is an alkyl group having 1 to 6 carbon atoms. Preferably R is a methyl group.

The lower alkyl esterified saccharides can be represented by the general formula

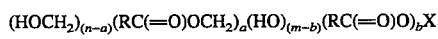

where R is an alkyl group having 1 to 6 carbon atoms, X represents the saccharide backbone, n is the number of hydroxyl groups on the primary carbons in the unesterified saccharide backbone, m is the number of hydroxyl groups on the secondary carbons of the unesterified saccharide backbone, a is the number of lower alkyl ester groups on primary carbons in the partially esterified saccharide, b is the number of lower alkyl ester groups on secondary carbons in the partially esterified saccharide. The lower alkyl esterified saccharide may have one or all hydroxyl groups replaced by lower alkyl ester groups. In other words, the value of the sum (a+b) in the formula of the esterified saccharide is at least about 1; preferably, (a+b) is at least about 2.

It is generally preferred that the polyol-type reagent is treated to significantly reduce the moisture content. In addition, it is generally preferred that the free organic acid content of the esterified saccharide is reduced before transesterification. Conventional methods to remove moisture and free organic acids can be used. One preferred technique whereby water and free organic acids are removed in a single step is freeze drying.

The saccharide starting materials for the present invention can be monosaccharides, disaccharides, and higher polysaccharides. Suitable monosaccharides include fructose, glucose, galactose, mannose, ribulose, rhamnose, xylulose, xylose, ribose, and arabinose; glucose is the preferred monosaccharide. Suitable disaccharides include melibiose, lactose, maltose, sucrose, trehalose, and cellobiose; sucrose is the preferred disaccharide. Suitable higher polysaccharides include raffinose, gentianose, 4'-galactosyl lactose, trisaccharides of galactose, mannose, glucose, and fructose, stachyose, verbascose, maltodextrins, corn syrup solids, zylans, glycogen, cellulose, amylose, agarose, galactans, and mananas. Sucrose, a non-reducing disaccharide, is the most preferred starting saccharide.

The saccharide starting materials may optionally be converted to the esterified saccharide by esterifying at least one of the hydroxyl groups of the saccharide starting materials using conventional methods. For example, sucrose can be partially esterified by reacting with acetic acid and an acid catalyst such as p-toluenesulfonic acid at about 100° C. for about three hours to form a mixture consisting mainly of sucrose diacetate and sucrose triacetate. Most preferably, sucrose can be completely esterified by using the method described by T. D. Mann et al. in *Journal of Chemical Education*, 69:8, p. 668 (1992) "Preparation of Sucrose Octaacetate—A Bitter Tasting Compound." Other esterification catalysts can also be used. Suitable acid catalysts for the initial esterification step include, for example, p-toluenesulfonic acid, phosphoric acid, polyphosphoric acid, phosphorous pentoxide, sulfuric acid, stannous chloride, zinc oxide, and the like. In the initial esterification step, the acid catalyst is generally used in an amount less than about 5 weight percent and preferably in the range of about 0.5 to 2.5 weight percent. Generally, the initial esterification step can be carried out at a temperature of about 70° to 95° C. Complete esterification can normally be achieved by reaction times on the order of about 0.5 to 1 hours. The esterification reaction process can be followed using, for example, thin layer chromatography or liquid chromatography. After removing excess acetic acid, the lower alkyl esterified saccharide is generally ready for use in the next transesterification step. It is generally preferred, however, that the free organic acid content of the lower alkyl esterified saccharide is reduced to below about 0.25 weight percent, more preferably below about 0.1 weight percent, and most preferably below about 0.05 weight percent.

Other polyol-type reagents, including polyols and saccharides, partially esterified polyols and saccharides, and fully-esterified polyols and saccharides, can also be employed in essentially the same manner. Preferred polyol-type reagents include partially-esterified and fully-esterified saccharides having lower alkyl ester groups. Partially-esterified saccharides preferably have at least 33 percent, and more preferably at least 66 percent, of the hydroxyl groups of the starting saccharide replaced with lower alkyl ester groups. The most preferred polyol-type reagents are the partially-esterified and fully-esterified sucroses having lower alkyl ester groups. One advantage to using partially- or fully-esterified saccharides is that they generally allow the formation of a homogenous reaction mixture with the fatty acid-containing reagents in the fatty acid transesterification step at the reaction temperatures employed.

Preferably, fully-esterified saccharides are derived from sucrose and have eight ester groups of the general formula —OOCR, where R is an aliphatic group containing from 1 to 6 carbon atoms, attached to the sucrose backbone in place of the hydroxyl groups. Preferably, R is a methyl group (i.e., the ester group is acetate). The most preferred esterified saccharide is derived from sucrose and contains eight acetate groups: sucrose octaacetate.

The fatty acid-containing reagents used in the present invention include fatty acids, fatty acid salts, lower alkyl esters of fatty acids, fatty acid anhydrides and fatty acid halides. The fatty acids employed in the present invention are of the general formula R'COOH where R' is a saturated or unsaturated aliphatic group generally containing from 3 to about 24 carbon atoms. The fatty acid salts employed in the present invention are of the general formula $R'COO^-Y^+$ where R' is as described above and Y is a cation selected from the group consisting of sodium, potassium, magnesium, calcium, and the like.

The fatty acid lower alkyl esters employed in the present invention are of general formula R'COOR" where R' is as described above and R" is a lower alkyl group having from 1 to about 6 carbon atoms. The fatty acid anhydrides employed in the present invention are of the general formula $(R'CO)_2O$ where R' is as described above; the two R' groups in the fatty acid anhydride can be the same or different. The fatty acid halides employed in the present invention are of the general formula R'Z where R' is as described above and Z is a halide; preferably Z is chlorine or bromine. Preferably, R' in the fatty acid-containing reagent is a long chain saturated or unsaturated aliphatic group containing between about 8 to 24 carbon atoms and, most preferably, R' is a long chain saturated or unsaturated aliphatic group containing between about 12 to 22 carbon atoms. Preferably R" is a methyl group. Preferably Y is a sodium or potassium cation.

The fatty acid lower alkyl esters, the fatty acid lower alkyl ester salts, the fatty acid anhydrides, and the fatty acid halides are preferably derived from the corresponding fatty acids. Examples of suitable fatty acids for use directly as fatty acid-containing reagents and for forming the other fatty acid-containing reagents include butyric, caproic, caprylic, capric, lauric, myristic, myristoleic, palmitic, palmitoleic, stearic, oleic, ricinoleic, linoleic, oleosteric, arachidic, behenic, erucic, arachidonic, and lignoceric acids. Generally fatty acids containing between about 14 and 18 carbon atoms are preferred since they are liquid at the reaction temperature and the corresponding fatty acid-containing reagents formed therefrom have minimal volatility at the reaction temperature and conditions employed in the esterification reaction. Pure fatty acids, naturally-occurring fats and oils (such as, for example, found in soybean, safflower, corn, peanut, and cottonseed oils), or partially hydrogenated fats and oils can be used. The fatty acids can be converted to the other corresponding fatty acid reagents using conventional methods. Both single fatty acid-containing reagents and mixtures of fatty acid-containing reagents may be employed in the present invention. A preferred reagent is fatty acid methyl ester. An alternative reagent is naturally occurring fat or triglyceride. Preferred fatty acids include stearic acid, oleic acid, palmitic acid, lauric acid, linoleic acid, and mixtures thereof. Preferred fatty acid lower alkyl esters include methyl stearate, methyl oleate, methyl palmitate, methyl laurate, methyl linoleate, and mixtures thereof. Preferred salts of fatty acid include the sodium and potassium salts of stearic acid, oleic acid, palmitic acid, lauric acid, linoleic acid, and mixtures thereof. Preferred fatty acid anhydrides include stearic acid, oleic acid, palmitic acid, linoleic acid, and mixtures thereof. Preferred fatty acid halides include steroyl chloride.

Preferably, the fatty acid-containing reagent is selected from the group consisting of fatty acids and fatty acid esters. When fatty acid anhydrides are employed, they are preferably used in combination with the fatty acids and/or fatty acid esters.

Generally, the fatty acid-containing reagent and the polyol-type reagent are present in the transesterification reaction mixture at a molar ratio of at least about 4 to 1 and preferably at a molar ratio of between about 6 to 1 and 15 to 1. Of course, the desired molar ratio will vary with different polyols or saccharides because of the different number of ester and hydroxyl groups present. More preferably, the amounts of esterified saccharide and the fatty acid-containing reagent in the reaction mixture are adjusted so the molar ratio of the contained fatty acid groups in the fatty acid-containing reagent to the esterified saccharide is about equal to the number of available ester and hydroxyl groups in the esterified saccharide. For example, when using esterified sucrose octaacetate the molar ratio of the fatty acid-containing reagent to the completely esterified saccharide would preferably be about 8 to 1 (i.e., approximately one fatty acid-containing reagent molecule for each available ester in the saccharide). Higher molar ratios can be used if desired within the general guidelines provided above.

The catalysts used for the esterification and transesterification reactions include both acid and base transesterification catalysts. Suitable acid catalysts include p-toluenesulfonic acid, phosphoric acid, polyphosphoric acid, phosphorous pentoxide, sulfuric acid, stannous chloride, zinc oxide, and the like. Suitable base catalysts include alkali metals, alkali metal carbonates, alkaline earth carbonates, alkali metal hydrides, alkaline earth hydrides, alkali metal alkoxides, and alkaline earth alkoxides. Generally, acid catalysts are used when the polyol-type reagent is reacted with fatty acids or fatty acid anhydrides. Generally, base catalysts are used when the polyol-type reagent is reacted with fatty acid esters. Generally, both acid and base catalysts can be used with salts of fatty acids realizing, of course, that under acidic conditions, the salts will be converted to the corresponding fatty acids.

Preferred alkali metal catalysts include sodium and potassium metal. Preferred alkali metal alkoxide catalysts include sodium and potassium alkoxides, including potassium methoxide, sodium methoxide, potassium ethoxide, sodium ethoxide, potassium t-butoxide, and sodium t-butoxide. Sodium methoxide is generally the most preferred alkali metal alkoxide catalyst. Preferred alkali metal carbonate catalysts include sodium carbonate, potassium carbonate and lithium carbonate. Preferred alkaline earth hydrides include calcium hydride. Mixtures of base catalysts can also be used if desired. For example, using sodium methoxide and calcium hydride in combination generally provide saccharide fatty acid polyesters having better color properties.

In the esterification and transesterification reactions, the acid or base catalyst is generally used in an amount less than about 5 weight percent and preferably in the range of about 0.5–2.5 weight percent. For the highest product yields, the catalyst should be freshly prepared.

The esterification reaction mixture formed from the basic starting materials (polyol-type reagent, fatty acid-containing reagent, and catalyst) should be essentially anhydrous. Additionally, as noted above, the esterified saccharide preferably is essentially free of organic acids. The esterification reaction itself is also carried out under essentially anhydrous conditions. Conventional means can be used to insure the required essentially anhydrous reactants and conditions. For example, reactants can be vacuum dried and stored over phosphorous pentoxide or other drying agents. A moisture scavenger such as a zeolitic molecular sieve may be added to the reaction to remove any excess moisture. The partially or completely esterified saccharide can be freeze-dried to remove both water and free organic acids. The reaction apparatus can be dried by flushing with dried, inert gases.

In the esterification and transesterification reactions, the reactants (polyol-type reagent and fatty acid-containing reagent) and catalyst are mixed in a reaction vessel and then heated to the reaction temperature (about 95° to 200° C. and preferably about 95° to 130° C.). In the improved method of the invention, as the esterification reaction proceeds, the relatively low molecular weight, non-fatty acid-containing lower alkyl ester by-product and/or alcohol by-product are removed by thin film reaction techniques to drive the equilibrium esterification reactions to completion.

Since the relatively low molecular weight ester by-product and alcohol by-product are removed (preferably continuously) during the esterification reactions to drive the equilibrium towards the desired polyol fatty acid polyester, the reactants are preferably selected so that the relatively low molecular weight ester by-product and alcohol by-product (i.e., methyl acetate and methanol) are relatively volatile and, thus, can be removed relatively easily from the reaction mixture.

The improved method of this invention provides that the low molecular weight by-products are removed from the reaction mixture using a thin film reaction technique. A thin film reaction technique is any method in which the reaction is conducted in a reaction mixture which is maintained in the form of a film which is from about 0.1 to about 5 mm thick, and preferably from about 0.5 mm to about 2 mm thick. For example, such thin films may be obtained by using a rotating flask, by flowing the reaction mixture on a vertical surface, or by spreading the reaction mixture over a reaction surface using a wiper blade or blades. In each of these methods, the reaction mixture is maintained in a thin film by gravity or other force which spreads the liquid reaction mixture out over a given surface.

One preferred method of removing the by-product ester and/or by-product alcohol is to rotate the reaction mixture on a reactor shell while drawing a vacuum over the reaction mixture. In utilizing this method, the reaction mixture is maintained in a thin film by the force of gravity causing the liquid to flow down the side of the flask as the rotator flask rotates. Alternatively, the by-product ester and/or alcohol may be removed by rotating the reaction mixture in a rotator flask or reactor shell while stripping or sparging with a suitable inert gas such as nitrogen, argon, or the like. It is preferred that the rotator flask be exposed to the inert atmosphere before the reactants are added to the rotator flask. Generally, as noted above, the reaction temperature for the transesterification step is in the range of about 95° to 200° C. Preferably, the reaction temperature for the transesterification step is in the range of about 95° to 130° C. The rotator flask may be raised to the preferred temperature using conventional techniques, including heated oil or water baths, electric jackets, and the like.

An alternative embodiment for the removal of the non-fatty acid-containing lower alkyl ester and/or alcohol by the thin layer reaction method is by using a wiper blade or blades to sweep the reaction mixture over a surface under vacuum or with an inert gas passing over the surface. This provides a short path for the transport of the volatile by-products in order to reduce their concentration in the reaction mixture.

Yet another embodiment wherein the ester and/or alcohol by-product is removed is one in which the reaction is under vacuum or there is inert gas passing over the thin film reaction as it is continuously pumped onto and flows down a vertical reaction surface. Such use of a vertical reaction surface permits a short path for the volatile by-product to be removed from the reaction mixture.

When using vacuum to remove the by-product ester and alcohol, it is generally preferred that the pressure is less than about 500 mm Hg, more preferably less than about 250 mm Hg, more preferably less than about 15 mm Hg, and most preferably less than about 1 mm Hg. When using inert gas sparging, the pressure can be at atmospheric pressure as well as below or above atmospheric pressure. Most preferably, the reaction is run under an inert, reduced-pressure, stream of nitrogen or argon at a vacuum lower than about 1 mm Hg. It is also generally preferred that the vacuum and inert atmosphere be initiated before the reactants are heated to the desired reaction temperature.

It is desired that the transesterification reaction be continued until sufficient conversion of the polyol-type reagent to the desired polyol fatty acid polyester has occurred. Generally a reaction time of about four hours will result in an 80 to 99 percent conversion to the desired product.

Generally, the polyol fatty acid polyesters produced by this invention are useful as fat substitutes or low-calorie fats. It is generally preferred that essentially all of the ester and hydroxyl groups in the saccharide are replaced with fatty acid ester groups in the saccharide fatty acid polyesters. For example, it is preferred that a sucrose fatty acid polyester produced by the method of this invention be composed mainly of sucrose having about eight fatty acid ester groups.

Once the transesterification reaction is completed, the reaction mixture is allowed to cool and the saccharide fatty acid polyester is collected and, if desired, purified. Conventional purification techniques can be used. It is generally preferred that the reaction mixture is first neutralized (using, for example, acetic acid), dissolved in an organic solvent (for example, hexane), and treated with activated carbon. Alternatively, the saccharide fatty acid polyester can be decolorized using hydrogen peroxide.

The polyol and saccharide fatty acid polyesters of the present invention are especially useful as fat substitutes or low-calorie fats in food products intended for human consumption. These polyol or saccharide fatty acid polyesters may be blended or incorporated into food compositions to reduce the overall calorie content of prepared food product. Liquid, semi-solid, or solid saccharide fatty acid polyesters (or combinations thereof) may be employed as fat substitutes. The solid saccharide fatty acid polyesters (i.e., melting points above about 37° C.) may also function as anti-anal leakage agents for use with the liquid saccharide fatty acid polyesters of this invention.

EXAMPLE

Sucrose octaacetate (4.72 g; 7 millimoles) was mixed with soybean-derived mixed fatty acid methyl esters (24.74 g; 85 millimoles) and sodium methoxide (0.6 g). In addition, a 5A zeolitic molecular sieve was added as a moisture scavenger. The reaction mixture was reacted in a rotator flask at 236 RPM while immersed in an oil bath maintained at 130° C. A continuous purge of dry nitrogen gas was introduced into the vapor space of the reactor at the rate of 1 liter/min. The reaction mixture was dispersed as a film of approximately 1 millimeter thickness on the wall of the reactor. The reaction was maintained in batch mode for four hours, after which the reactor contents were cooled and neutralized with $H_3PO_4$ (0.66 g; 85%). Using size exclusion chromatography, the hexane solubles were found to contain approximately 36.7% residual fatty acid methyl esters, and 63.3% sucrose fatty acid polyesters. Using mass spectrometric analysis, the sucrose fatty acid polyester fraction was found to contain about 62% of sucrose fatty acid octaester. A similar sucrose fatty acid polyester preparation using the same reagents and reaction conditions, except carried out in a bulk, non-thin film reaction vessel, would be expected to have a sucrose fatty acid octaester content of only about 45 to 50 percent.

What is claimed is:

1. A method for making a polyol fatty acid polyester comprising:
   (1) mixing a polyol-type reagent, a fatty acid-containing reagent, and an esterification catalyst under essentially anhydrous conditions to form a reaction mixture; and
   (2) heating the reaction mixture to about 95° to 200° C. for a time sufficient to form the polyol fatty acid polyester while removing non-fatty acid-containing lower alkyl ester by-product or alcohol by-product from the reaction mixture wherein the reaction mixture is maintained in a thin film to facilitate removal of the by-product.

2. A method as defined in claim 1, wherein the polyol-type reagent is a polyol or saccharide containing hydroxyl groups.

3. A method as defined in claim 1, wherein the polyol-type reagent is a partially-esterified polyol or saccharide containing hydroxyl groups and lower alkyl ester groups.

4. A method as defined in claim 1, wherein the polyol-type reagent is a fully-esterified polyol or saccharide containing lower alkyl ester groups.

5. A method as defined in claim 1, wherein the polyol-type reagent is sucrose or sucrose octaacetate.

6. A method as defined in claim 1, wherein the thin film is formed by rotating the reaction mixture on a reactor shell.

7. A method as defined in claim 1, wherein the thin film is formed with a wiper blade sweeping the reaction mixture over a surface.

8. A method as defined in claim 1, wherein the thin film is formed by flowing the reaction mixture over a surface of a vertical reactor.

9. A method as defined in claim 1, wherein the thin film is contacted with a purge of inert gas at reduced pressure to assist in removing the by-product.

10. A method for making a saccharide fatty acid polyester comprising:
    (1) esterifying one or more hydroxyl groups of a saccharide to form a partially-esterified saccharide having at least one lower alkyl ester group or a fully-esterified saccharide having lower alkyl ester groups;
    (2) mixing the partially-esterified saccharide or fully-esterified saccharide, a fatty acid-containing reagent, and an esterification catalyst under essentially anhydrous conditions to form a reaction mixture; and
    (3) heating the reaction mixture to about 95° to about 200° C. for a time sufficient to form the saccharide fatty acid polyester while removing a non-fatty acid-containing lower alkyl ester by-product or alcohol by-product from the reaction mixture, wherein the reaction mixture is maintained in a thin film to facilitate removal of the by-product.

11. A method as in claim 10, wherein the saccharide is esterified to form a partially-esterified saccharide having at least 33% of its hydroxyl groups replaced by lower alkyl ester groups.

12. A method as in claim 10, wherein the saccharide is esterified to form a partially-esterified saccharide having at least 66% of it hydroxyl groups replaced by lower alkyl ester groups.

13. A method as in claim 10, wherein the saccharide hydroxyl groups are esterified to form a fully-esterified saccharide having lower alkyl ester groups.

14. A method as in claim 13, wherein the fully-esterified saccharide is sucrose octaacetate.

15. A method as in claim 10, wherein the thin film is formed by rotating the reaction mixture on a reactor shell.

16. A method as in claim 10, wherein the thin film is formed with a wiper blade sweeping the reaction mixture over a surface.

17. A method as in claim 10, wherein the thin film is formed by flowing the reaction mixture over a surface of a vertical reactor.

18. A method as in claim 10, wherein the thin film is contacted with a purge of inert gas at reduced pressure to assist in removing the by-products.

19. A method as in claim 14, wherein the thin film is contacted with a purge of inert gas at reduced pressure to assist in removing the by-product.

20. A method for making a sucrose fatty acid polyester comprising:
    (1) esterifying one or more hydroxyl groups of sucrose to form a partially-esterified sucrose having at least one lower alkyl ester group or a fully-esterified sucrose having lower alkyl ester groups;
    (2) mixing the partially-esterified sucrose or fully-esterified sucrose, a fatty acid-containing reagent, and an esterification catalyst under essentially anhydrous conditions to form a reaction mixture; and
    (3) heating the reaction mixture to about 95° to about 200° C. for a time sufficient to form the sucrose fatty acid polyester while removing a non-fatty acid-containing lower alkyl ester by-product or alcohol by-product from the reaction mixture, wherein the reaction mixture is maintained in a thin film by rotating the reaction mixture on a reactor shell, by sweeping the reaction mixture with a wiper blade over a surface, or by flowing the reaction mixture over the surface of a vertical reactor.

21. A method as in claim 20, wherein the thin film is contacted with a purge of inert gas at reduced pressure to assist in removing the by-product.

* * * * *